(12) United States Patent
Boston

(10) Patent No.: US 6,347,941 B1
(45) Date of Patent: *Feb. 19, 2002

(54) PARTIAL DENTIN CARIES EXCAVATOR

(75) Inventor: Daniel W. Boston, St. Davids, PA (US)

(73) Assignee: Temple University of the Commonwealth System of Higher Education, Philadelphia, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/792,711

(22) Filed: Feb. 23, 2001

(51) Int. Cl.[7] .............................. A61C 3/02; A61C 3/06
(52) U.S. Cl. ........................................ 433/165; 433/166
(58) Field of Search ............................ 433/125, 165, 433/166, 229

(56) References Cited

U.S. PATENT DOCUMENTS

| | | |
|---|---|---|
| 463,919 A | 11/1891 | Burdick |
| 503,744 A | 8/1893 | How |
| 1,225,230 A | 5/1917 | Elwin |
| 1,636,577 A | 7/1927 | Schuller |
| 4,190,958 A | 3/1980 | Martin et al. |
| 4,283,175 A | 8/1981 | Nash |
| 4,365,958 A | 12/1982 | Vlock |
| 4,449,937 A | 5/1984 | Weissman |
| 4,661,061 A | 4/1987 | Martin |
| 4,684,346 A | 8/1987 | Martin |
| 4,709,480 A | 12/1987 | Takigawa et al. |
| 5,017,137 A | 5/1991 | Weissman |
| 5,035,618 A | 7/1991 | Katz et al. |
| 5,299,937 A | 4/1994 | Gow |
| 5,601,430 A | 2/1997 | Kutsch et al. |
| 5,636,983 A | 6/1997 | Shoji et al. |
| 5,676,593 A | 10/1997 | Stevens |
| 6,106,291 A | 8/2000 | Boston |

FOREIGN PATENT DOCUMENTS

DE     2 303 148     7/1974

OTHER PUBLICATIONS

Clifford M. Sturdevant, et al., "Rotary Cutting Instruments," *The Art and Science of Operative Dentistry,* Third Edition, pp. 345–352 (1995).
"Surgical Carbide Burs," Advertisement for Karl Schumacher Dental Instrument Co. (1998).
T. Fusayama, "Two Layers of Carious Dentin: Diagnosis and Treatment," *Operative Dentistry,* vol. 4, pp. 63–70 (1979).
C. W. Sturdevant, "Art and Science of Operative Dentistry", *Mosby, St. Louis;* Third Edition, pp 94–101, pp. 313–352 (1995).
T. Fusayama et al., "Relationship between Hardness, Discoloration, and Microbial Invasion in Carious Dentin", *Journal of Dental Research,* pp. 1033–1046 (1966).

*Primary Examiner*—Nicholas D. Lucchesi
(74) *Attorney, Agent, or Firm*—Ratner & Prestia

(57) ABSTRACT

A dental bur for use in repair of a carious lesion has a working surface including cutting elements which deflect or abrade upon encountering material having a hardness at or above a preselected hardness, wherein said preselected hardness is below the hardness of normal dentin and is generally below a hardness corresponding to the lower limit of hardness of pre-carious dentin to be retained in painless procedures.

6 Claims, 4 Drawing Sheets

PARTIAL DENTIN CARIES EXCAVATOR

FIELD OF THE INVENTION

This invention relates generally to the field of dental cutting tools and to a method for minimizing pain associated with the repair of dental caries. More specifically the invention relates to a dental bur that, independently of operator control, removes primarily carious dentin having a preselected hardness without removing normal dentin or significant amounts of pre-carious dentin, or any dentin having a hardness above the preselected hardness value.

BACKGROUND OF THE INVENTION

Dental caries involve infectious microbiological disease wherein the infection results in localized dissolution and destruction of calcified tooth structures. When the lesion extends beyond the enamel or cementum to the underlying dentin, various changes occur in the dentin. In general, these changes are depth dependent. For example, bacterial infection tends to be higher in the superficial layers of dentin, i.e. those closest to the surface of the tooth (the dentin in those layers being hereinafter referred to as 'carious dentin'), whereas deeper layers of dentin have lower levels of infection or may not be infected at all (the dentin in those layers being hereinafter referred to as 'pre-carious dentin'). In addition, the superficial layers of carious dentin are greatly softened, and the hardness of the dentin gradually increases with the depth of the dentin until a level is reached where the dentin is of normal hardness. Thus, between the extremes of carious dentin (highest level of infection and lowest hardness) and that of normal dentin (no infection and highest hardness) is pre-carious dentin (low or no infection and intermediate hardness).

In most instances, it is medically advisable to remove substantially all carious dentin to ensure that the lesion does not expand, and to provide a good mechanical foundation for the restoration material. Removal of pre-carious dentin is not medically necessary in most instances because it is minimally or not at all infected (and thus does not pose significant danger of the lesion expanding), and also because its hardness is sufficient to provide a good mechanical foundation for the restoration material. Since carious dentin is not sensitive but pre-carious dentin is sensitive, a procedure that removes some or all carious dentin but does not remove most pre-carious dentin can be substantially pain-free while medically sound.

There are many common dental instruments used for removing carious dentin from teeth. Typically, however, high speed burs or other excavation tools are used to excavate the carious dentin. Unless the operator senses when a harder material is encountered and immediately ceases drilling, prior art burs will continue to cut through both carious dentin and pre-carious dentin into normal dentin during and after removal of the carious dentin. Because of the difficulty in sensing precisely when harder material is encountered, the side effect of using such a bur is cutting of pre-carious dentin and some cutting of normal dentin. In addition, this produces an infected and clogged bur that is relatively expensive to discard and difficult to sterilize.

U.S. Pat. No. 6,106,291 describes and claims a bur which is designed to deflect, deform or abrade upon encountering dentin having a preselected hardness corresponding to the lower limit of hardness for non-carious (i.e., normal) dentin. Thus, the bur is designed to cut through both carious and pre-carious dentin, but to deflect or abrade when it reaches normal dentin, and to do so independently of operator control. Such a bur avoids inadvertent and unnecessary removal of normal dentin, but does not distinguish between the carious dentin which must be removed to provide a sound base for placing a restoration and the pre-carious dentin which need not be removed during restoration. Nor does such a bur distinguish between various levels of hardness of carious dentin in those clinical procedures requiring only partial removal of carious dentin, for example, indirect pulp cap procedures.

The present invention provides an improved dental cutting tool which deflects, deforms or abrades when encountering material having a preselected hardness below the lower limit of hardness of normal dentin. Thus, the bur of this invention is capable of selectively differentiating between softer carious dentin having various levels of hardness and between carious dentin and harder pre-carious dentin, substantially irrespective of operator control. Further, by selecting a bur having a preselected hardness such that it deforms, deflects or abrades upon encountering material having a hardness corresponding to or lower than the lower limit of hardness of pre-carious dentin, thereby minimizing or eliminating the removal of pre-carious dentin, a restoration can frequently be accomplished painlessly or with minimal dental discomfort and without need for anesthesia.

SUMMARY OF THE INVENTION

The dental cutting tool (or "bur") of the present invention has a working surface that includes cutting elements adapted to deflect, deform, or abrade when encountering a material of hardness above a preselected value, wherein the preselected value is less than the lower limit of hardness of normal dentin. As a corollary, the preselected hardness may also be referred to as the bur's 'cutting hardness,' reflecting the fact that the bur will cut or drill selectively only material of less than the preselected hardness. Since a bur is selected having a cutting hardness which is less than the lower limit of hardness of normal dentin, the bur will excavate all carious and/or pre-carious dentin having a hardness below the preselected value. When dentin of hardness above the bur's cutting hardness is encountered, the cutting elements deflect, deform, or abrade, thus preventing damage to or removal of the harder dentin. More particularly, the present invention provides a dental bur with a cutting hardness in the range of about 1 to about 40 Knoop Hardness Number (KHN), whereas the lower limit of hardness for normal dentin is characteristically at or above about 50 KHN or 60 KHN. In a preferred embodiment, the bur's cutting hardness is preselected at or slightly below the lower limit of hardness for pre-carious dentin, thus permitting painless repair of a carious lesion while removing most carious dentin. In a further embodiment, the bur's cutting hardness is preselected at a value below the lower limit of hardness of pre-carious dentin, thereby permitting only partial removal of carious dentin for procedures such as indirect pulp cap. Thus, by selecting a bur of appropriate cutting hardness below the hardness of normal dentin, one may remove all or a portion of carious dentin and, optionally, a portion but not all of pre-carious dentin, thereby preventing removal of or damage to normal dentin.

BRIEF DESCRIPTION OF THE DRAWING

The invention is best understood from the following detailed description when read in connection with the accompanying drawings, in which.

DETAILED DESCRIPTION OF THE INVENTION

Figure 1:
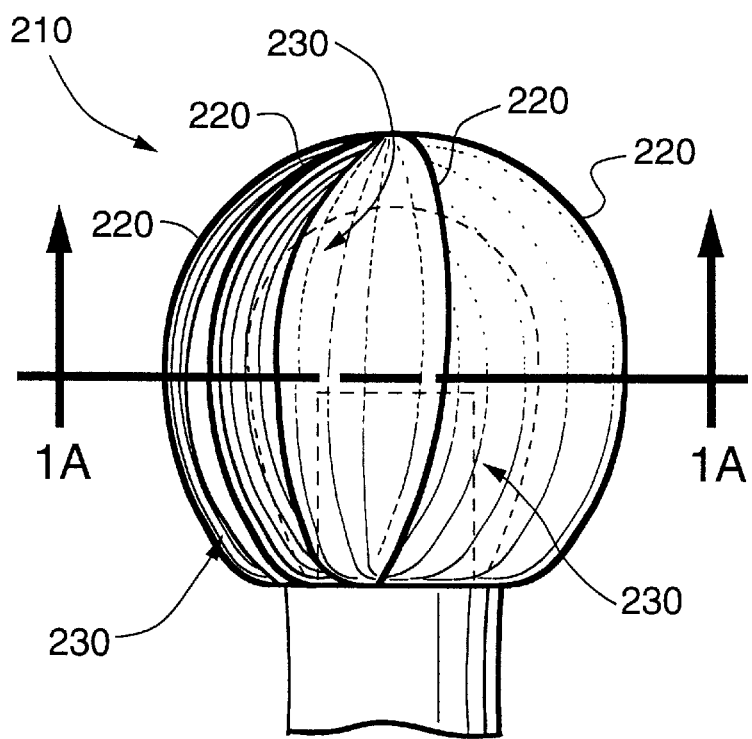
FIG. 1 is a side view of a dental bur formed according to a first exemplary embodiment of the present invention.
Figure 1A:
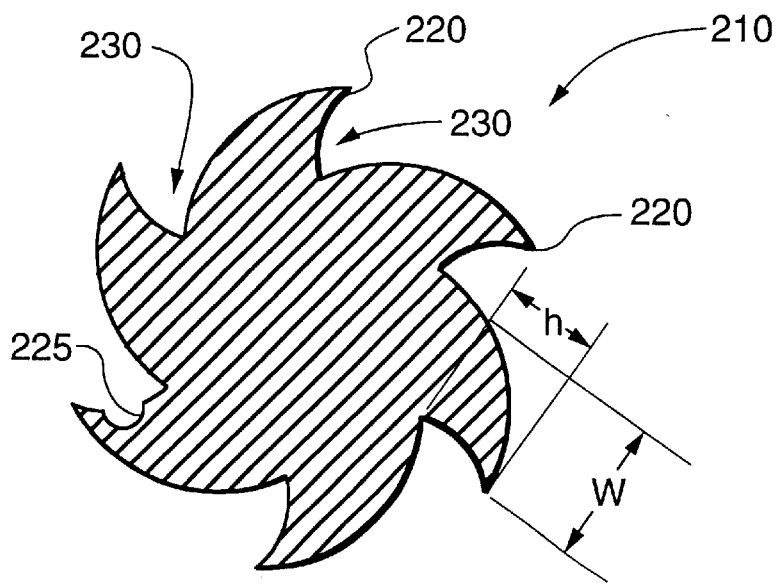
FIG. 1A is a sectional view, in the plane 1A—1A, of the bur shown in FIG. 1.

Referring now to the Figures, wherein like reference numerals refer to like steps and elements throughout, FIGS. 1 and 1A are side and sectional views, respectively, of the cutting head of a bur according to the first exemplary embodiment of the present invention. As shown in FIGS. 1 and 1A, bur 210 includes bur blades 220 interposed between grooves 230. Bur blades 220 are formed so that they will cut soft carious dentin, but will bend inward into the space of grooves 230 upon reaching a dentin of a specified higher hardness and render bur 210 temporarily or permanently inoperable. Optimally, blades 220 may include concavity 225 to effect better control of the deflection, deformation, and/or abrasion of blades 220 upon encountering dentin of hardness higher than the bur's cutting hardness.

The cutting hardness of the bur that is used may vary with different individual situations, patients, or patient groups and with different clinical indications. Generally, the lower level of hardness for normal dentin is at or above about 50 or 60 KHN, whereas pre-carious dentin generally has a hardness in the range of about 4 up to about 50 or 60 KHN, and carious dentin generally has a hardness in the range of about 1 to about 30 KHN. While the dentin hardness for each of these cases cannot be precisely defined, as it varies from patient to patient, it has been found that the bacterial content of carious dentin correlates well but not perfectly with alterations in the collagen matrix of carious lesions and can be indicated clinically by use of dentin caries dyes. Use of such dyes enables one to identify and distinguish between carious material which is highly infected and must be removed and deeper carious or pre-carious material which is only lightly infected or not sufficiently infected to require removal. Further presence or absence of pain experienced by the patient during repair of carious lesions also correlates with the alterations that occur in the dentin collagen matrix, as disclosed with dentin caries dyes. Generally, carious dentin is dye stainable and is not sensitive to instrumentation during its removal, whereas pre-carious dentin is non-stainable and is sensitive and produces pain when dental instruments are applied during its removal.

Based on the foregoing and on available studies typical cut-off values for the maximum hardness of dentin cut by a bur having a given cutting hardness are provided in Table 1 below for painless removal of carious dentin for various clinical indications:

TABLE 1

| Cutting Hardness (KHN) | Typical Clinical Use |
| --- | --- |
| 1–2 | Painless conservative partial removal of highly infected dentin in indirect pulp cap |
| 2–5 | Painless aggressive partial removal of highly infected dentin in indirect pulp cap |
| 4–20 | Painless removal of highly infected carious dentin in acute lesions |
| 16–20 | Painless removal of highly infected carious dentin in chronic/smooth surface lesions |
| 20–25 | Painless removal of dye-stainable outer carious dentin |

While the foregoing table provides general guidelines for the bur's cutting hardness for painless removal of dentin for various indications, there are a number of modifying factors which indicate use of a bur or burs having a higher or lower cutting hardness. Table 2 below sets forth a number of common clinical findings and provides, for each of them, a range of values by which the values in Table 1 may be increased or decreased to assist in selecting a bur having a cutting hardness suitable for a particular type of restoration:

TABLE 2

| Increase Cutting Hardness | +KHN | Decrease Cutting Hardness | –KHN |
| --- | --- | --- | --- |
| Chronic Lesion | 5–20 | Very acute lesion | 1–10 |
| Very Hard Lesion | 5–20 | Very soft lesion | 1–10 |
| Highly stained lesion | 5–10 | Low pain threshold | 1–10 |
| Close to tooth surface | 10–30 | Close to pulp chamber | 1–10 |
|  |  | Primary tooth | 1–10 |

Further understanding of the use of these tables in a clinical situation is provided by reference to the following clinical example. In this example a dentist is presented with a lesion which he judges to be acute, highly infected carious dentin, thus indicating (from Table 1) use of a bur having a cutting hardness in the range of 4–20 KHN. Because the lesion is judged to be only moderately acute, the dentist may initially select from table 1 a bur having a cutting hardness of, for example, 10 KHN. The patient, however, is believed by the dentist to have a moderately low pain threshold, which from Table 2 provides for an adjustment (downward) in the initially selected cutting hardness by 1–10 KHN. Since the dentist wishes to minimize pain and make the restoration without anesthetic if possible, he selects a downward adjustment of 5 KHN. Thus, based on this quantitative approach, the dentist would initially preselect a bur having a cutting hardness, for example, of 5 KHN. However, it will be appreciated by those skilled in the art that the initial preselected cutting hardness will be determined less quantitatively and more qualitatively based on overall assessment of the clinical picture presented. It will also be appreciated that in many instances the initial preselection may need to be adjusted upward if the initially preselected bur ceases cutting before an adequate amount of carious material is excavated.

Thus, the blades (or cutting elements in other embodiments) of the present invention would be constructed so as to deflect, deform, or abrade upon encountering material above a preselected hardness, as generally determined in accordance with the foregoing guidelines. Accordingly, to perform painless excavation and repair of a carious lesion, a bur having a cutting hardness in the range of about 1 to about 30 KHN would be selected, thereby limiting cutting action to the margin between softer carious material and relatively harder pre-carious material of the lesion. However, one skilled in the art will appreciate that in certain clinical situations it may be desirable to remove a portion of the pre-carious material in addition to the carious material. Thus, it is contemplated that the bur may be designed to have a cutting hardness somewhat above that indicated above, for example up to 40 or 50 KHN, for use with patients having a normal dentin hardness at or above about 60 KHN. It will also be appreciated that for other situations a substantially softer bur, for example one with a cutting hardness in the range of 1–10 KHN, would be selected, particularly for procedures in which it was desired to remove some but not all of the carious material, for example, an indirect pulp cap procedure.

Skilled designers can readily design blades 220 so as to deflect at the preselected resistant force by proper selection of the material of construction of blades 220, and the dimensions thereof, particularly the height of each blade and the varying width of each blade. In addition, as indicated above, concavities 225 can be incorporated into the design of the blades 220 to optimize deflection or deformation at the preselected hardness.

The number of bur blades 220 can be increased or reduced according to design parameters. Similarly, the depth of grooves 230 can be varied and the surface area of bur blades 220 can be increased or decreased according to specific design parameters. For example, the number of bur blades 220 can be reduced and grooves 230 can be deepened to increase the scooping effect in soft dentin, and to decrease the efficiency of bur blades 220 as the bur approaches harder dentin.

Still another important design variable, which the skilled designer will optimize for optimum performance is concavity 225, the slope and depth of which may vary considerably. For example, an angular indentation may also perform this deflection-effecting function (i.e., to control the resistance level at which bur blade 220 will deflect).

Certain embodiments of bur blades 220 can recover to their initial shape after bending back into grooves 230 and may be available then to cut more superficial, softer carious dentin. These include silicone rubber and resilient, molded plastic embodiments. The ability to recover allows for removal of carious dentin by multiple vertical approaches. In other alternative embodiments of bur 210, constructed of aluminum, aluminum alloy, hard ceramic, and plastic, blades 220 will deform or abrade and be rendered inoperable.

The shape of blades 220 and grooves 230 may be better seen from the cross sectional view of bur 210 in FIG. 1A. Bur 210 may be manufactured by machining a relatively hard metal sphere, such as one comprised of aluminum or aluminum alloy. Alternatively, blades 220 may be separately formed and secured to an underlying base. In either case, blades 220 may be anchored through a shank to a central pin extending through blades 220 and the core.

The shank is standard sized, such as described in American National Standards Institute/American Dental Association (ANSI/ADA) Specification No. 23 (dental excavating burs). The shank may be constructed of steel, aluminum, or other suitable materials. Both latch type (Class 1-Angle handpiece) and friction grip (Class 4-Angle handpiece) shanks may be used in the excavator of the present invention. Bur 210 may also be injection molded from liquid silicone rubber for example.

The color of bur 210 can be made unique for each size bur and for each hardness level at which bur 210 is molded. This allows the user of bur 210 to identify quickly the desired size and hardness level of the bur needed. The head of the bur can be spherical or egg-shaped, having a diameter between about 0.6 mm and about 4.0 mm. In addition, the head can have alternative shapes that are compatible with the cutting elements of the present invention. The head can be made out of a variety of materials, including molded plastic, optionally polymethylmethacrylate, silicone rubber, wire ball, polymer wool, aluminum or aluminum alloy, cast alloy, and ceramic.

As an alternative to the design of blades 220 which deflect upon encountering a preselected resistance force, bur blades 220 may be composed of an abradable material, such as hard ceramic elements embedded in a resinous base, designed to fracture or release the ceramic element when the preselected resistance force is encountered. Bur 210 may also be machinable from a hard ceramic material or injection molded from plastic material.

Still other characteristics may be designed into blades 220 by increasing or decreasing the distance between consecutive blades 220 and, thus, enlarging or reducing the area of the grooves where blades 220 may retract.

Figure 2:
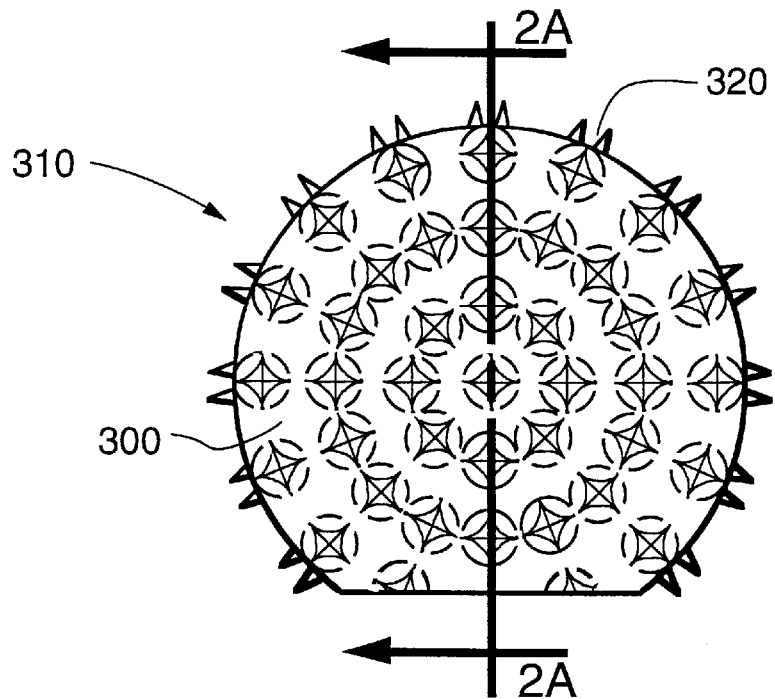
FIG. 2 is a side view of a bur formed according to a second exemplary embodiment of the present invention.
Figure 2A:
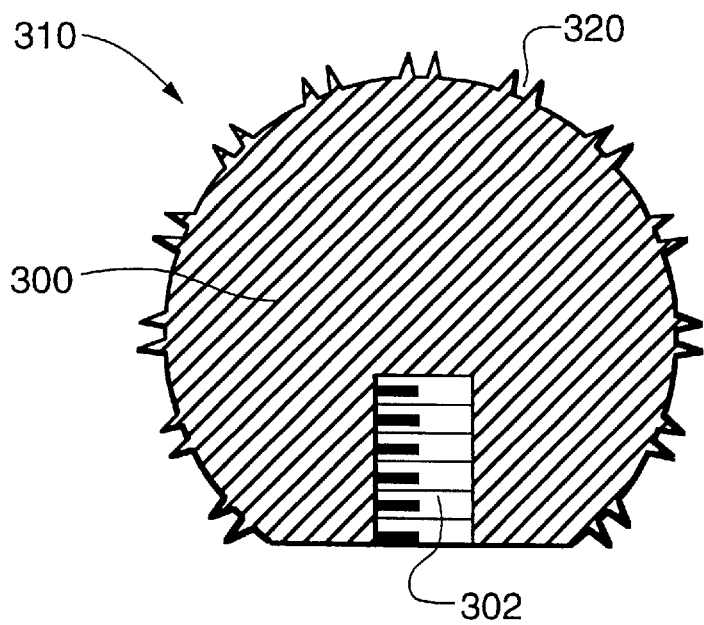
FIG. 2A is a sectional view, in the plane 2A—2A, of the bur shown in FIG. 2.
Figure 3:
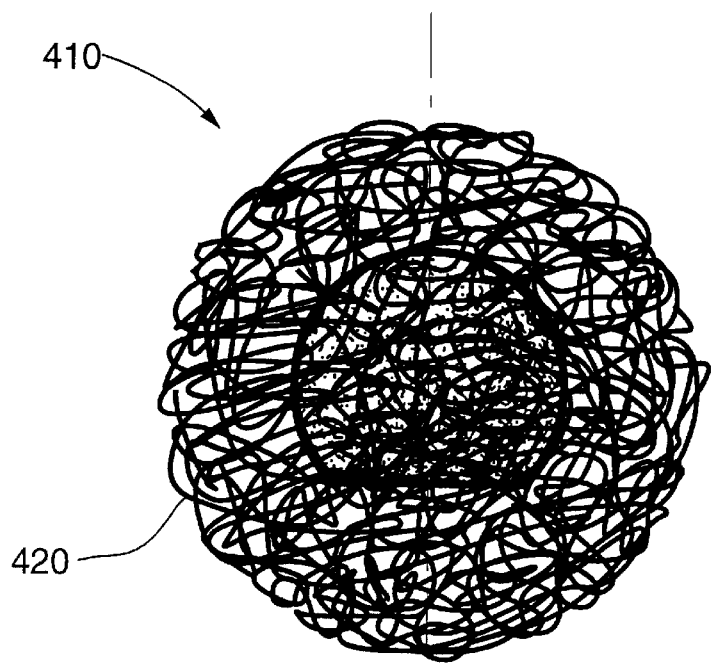
FIG. 3 is a side view of a bur formed according to a third exemplary embodiment of the present invention.
Figure 5:
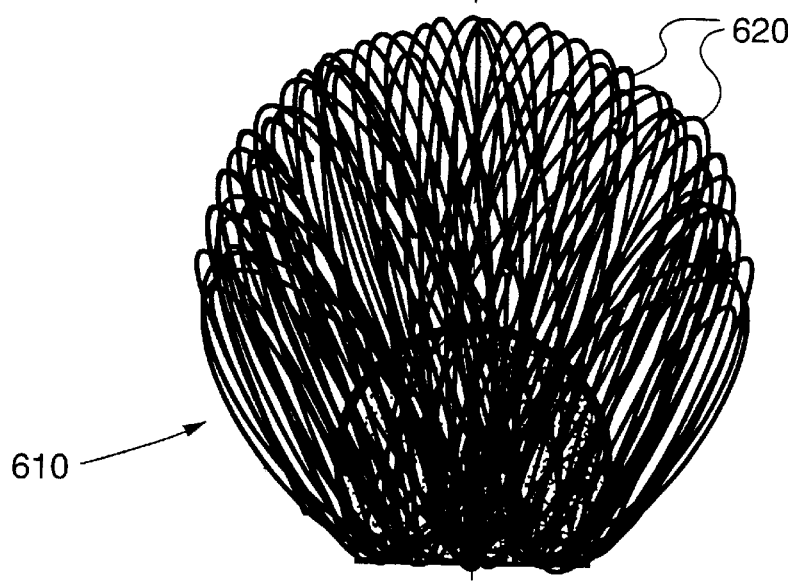
FIG. 5 is a side view of a bur formed according to a fifth exemplary embodiment of the present invention.
Figure 4:
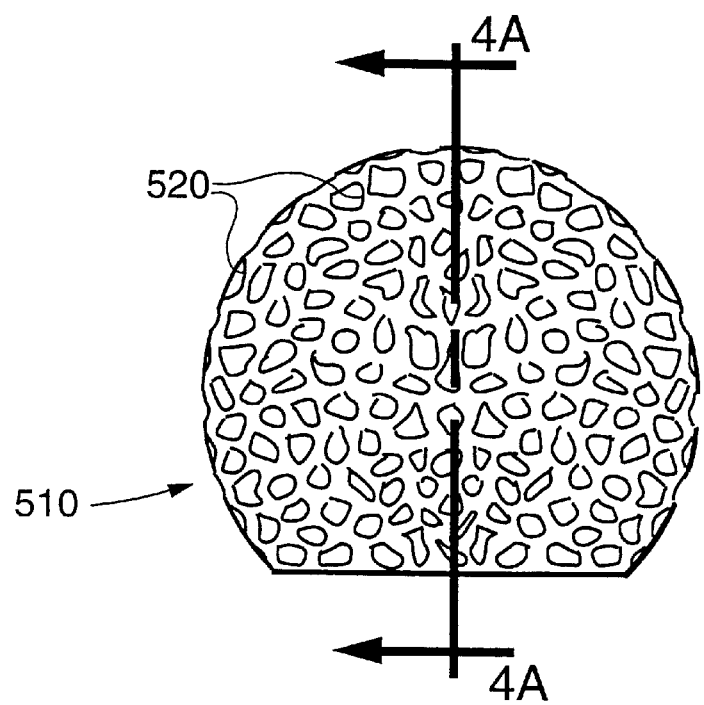
FIG. 4 is a side view of a bur formed according to a fourth exemplary embodiment of the present invention.
Figure 4A:
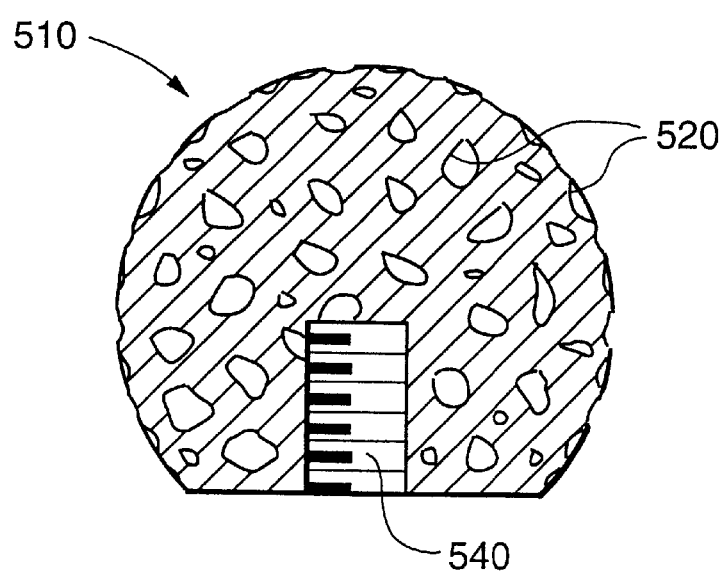
FIG. 4A is a sectional view, in the plane 4A—4A, of the bur shown in FIG. 4.

Still other alternative bur designs are shown, for example, in FIG. 2, a side view of bur 310 formed according to a second exemplary embodiment of the present invention, and in FIG. 2A, a cross section of bur 310 shown in FIG. 2. FIG. 3 shows bur 410 having wires 420 in a polymer wool ball. FIG. 4 shows bur 510 in a ball like structure and FIG. 4A shows a cross section of bur 510 shown in FIG. 4. FIG. 5 shows bur 610 also having wires 620 in an alternative ball like structure.

The burs shown in FIGS. 2–5 all vary in their mechanical design but each depends on the core concept of the present invention which is the use of cutting elements that either deflect, deform, or abrade upon encountering a preselected cutting resistance force which is below the hardness of normal dentin. For painless restorations, this force is characteristic of the differential force below which soft or carious dentin may be cut or drilled by the bur and at or below that required to cut or drill at the leading edge of pre-carious dentin.

These different mechanical forms of the present invention include, in FIGS. 2 and 2A, a ball like central element 300 with a threaded recess 302 for mounting the bur on a conventional dental drilling apparatus. Although not shown in the Figures, such a mounting recess would necessarily be included in all bur heads made of a different material than the shank, ie., machined ceramic, molded silicone rubber, wire ball, polymer wool ball, and ceramic foam versions. Moreover, the mounting recess is not necessary when the material for the entire excavator (blades, core, and shank) is the same, i.e., machined aluminum or aluminum alloy and molded plastic versions. As described above, the shank of the excavator would conform to ANSI/ADA specifications. The dental bur 310 of FIGS. 2 and 2A further includes outwardly punched projections 320 which serve as cutting elements. Like the cutting blades of bur 210 in FIG. 1, the outward projections 320 in bur 310, of FIGS. 2 and 2A, are mechanically designed to either deflect or abrade upon encountering dentin of preselected hardness. Such a design may easily be made by those skilled in the art by reference to the dimensions and the material used in the construction of the upstanding projections, constituting cutting elements 320 in the bur of FIGS. 2 and 2A.

In addition, the embodiments, as shown in FIGS. 3 and 5, comprise dental burs wherein the cutting elements, which may be disposed over a mounting ball as in previous embodiments, comprise relatively hard, wire-like cutting material 420, in FIG. 3, or material 620, in FIG. 5. The material is sufficiently resistant to deflecting and abrading to cut softer carious dentin material, but sufficiently deflectable or abradable so as to avoid cutting through the deeper, harder pre-carious layer or damaging healthy dentin material. This may be useful to avoid interruption of the cutting action in other burs in which narrow grooves in a bur 210 of the type shown in FIG. 1, or a more dense cutting material in a bur 510 of the type shown in FIG. 4, become fully loaded with carious dentin removed from the drilling surface, thus impeding a further cutting action. The cutting effectiveness of the wires shown in FIGS. 3 and 5 will be determined by the design factors of the shape resilience of the wire selected in relation to the cross section of the individual wire filaments, and the density of the bulk wire. This is a relationship of the space occupied by the wire itself versus the space occupied by the interstices surrounding the wire. Material selection will also be an important part of the design consideration in the development of cutting elements based on wire-like materials in accordance with these embodiments.

Still another embodiment of the present invention is that shown in FIGS. 4 and 4A, in which the dental bur 510 comprises a ball member with pores 520. The residual surrounding material of the pores 520 at the outer surface of the ball like bur 510 comprise cutting elements which, as in previous embodiments, are designed with respect to the material of construction and the dimensions. Ball like bur 510 also includes recess 540 for mounting bur 510 on a conventional dental drilling apparatus. A porous cutting bur 510 as shown in FIGS. 4 and 4A may also be designed specifically to provide sufficient porosity to retain carious dentin removed from the drilling surface so as to avoid interruption of the cutting process.

The partial caries dental excavator of this invention, because it is designed to deform, abrade, or deflect when it encounters material having a hardness below about 40 KHN and more suitably below about 30 KHN, is very soft and comprises cutting elements which are intended only for use in a slow speed handpiece. In general they are suitably employed after access to the lesion has been obtained using a high speed handpiece and bur. The burs of this invention are not intended for withstanding the forces of rotation provided by high speed handpieces. In particular, the design features of this invention are similar to the design features of the bur described in U.S. Pat. No. 6,106,291, with the exception that plastic, rubber, ceramic, metal or elastomer components are made of substantially softer material, cutting elements are designed with positive rake angles, acute edge angles and greater clearance angles to provide cessation of cutting at a lower hardness, fluting between cutting blades or spacing between cutting elements is increased to provide space for dislodged soft carious dentin, and wire cutting elements are of finer diameter and cross-sectional shape to facilitate termination of cutting at a lower hardness. Typical construction materials include but are not necessarily limited to polyamide-imide (Torlon™), acetal (Delrin™), Nitinol™ wire and many other commercially available polymers, metals, ceramics, and abrasives.

Although illustrated and described herein with reference to certain specific embodiments, the present invention is nevertheless not intended to be limited to the details shown. Rather, various modifications may be made in the details within the scope and range of equivalents of the claims and without departing from the invention.

What is claimed:

1. A dental bur for use in removing all or a portion of carious dentin and, optionally, a portion but not all of pre-carious dentin from teeth, said bur having a working surface including cutting elements, said cutting elements being adapted to deflect, deform, or abrade upon encountering material having a preselected hardness in the range of about 1 KHN to about 40 KHN, wherein said preselected hardness is less than the lower limit of hardness of normal dentin.

2. The dental bur according to claim 1, said cutting elements being adapted to deflect, deform or abrade upon encountering a material having a hardness above a preselected hardness, wherein said preselected hardness is in the range of about 1 KHN to about 5 KHN for painless partial removal of highly infected carious dentin in an indirect pulp cap procedure.

3. The dental bur according to claim 1, said cutting elements being adapted to deflect, deform or abrade upon encountering a material having a hardness above a preselected hardness, wherein said preselected hardness is in the range of about 4 KHN to about 20 KHN for painless removal of highly infected carious dentin in acute lesions.

4. The dental bur according to claim 1, said cutting elements being adapted to deflect, deform or abrade upon encountering a material having a hardness above a preselected hardness, wherein said preselected hardness is in the range of about 16 KHN to about 20 KHN for painless removal of highly infected carious dentin in chronic/smooth surface lesions.

5. The dental bur according to claim 1, said cutting elements being adapted to deflect, deform or abrade upon encountering a material have a hardness above a preselected hardness, wherein said preselected hardness is in the range of about 20 KHN to about 25 KHN for painless removal of dye-stainable pre-carious dentin.

6. The dental bur according to claim 1, said cutting elements being adapted to deflect, deform or abrade upon encountering a material having a hardness above a preselected hardness, wherein said preselected hardness is in the range of about 1 KHN to about 30 KHN corresponding to the lower limit of hardness of pre-carious dentin.

* * * * *